United States Patent [19]

Hackenbruch et al.

[11] Patent Number: 5,264,633
[45] Date of Patent: Nov. 23, 1993

[54] PROCESS FOR THE PREPARATION OF 1,4-BIS(4-HYDROXYBENZOYL)BENZENE

[75] Inventors: Joachim Hackenbruch, Mainz; Theodor Papenfuhs, Frankfurt am Main; Arnold Schneller, Mainz, all of Fed. Rep. of Germany

[73] Assignee: Hoechst Aktiengesellschaft, Frankfurt, Fed. Rep. of Germany

[21] Appl. No.: 854,658

[22] PCT Filed: Oct. 25, 1990

[86] PCT No.: PCT/EP90/01809

§ 371 Date: Apr. 29, 1992

§ 102(e) Date: Apr. 29, 1992

[87] PCT Pub. No.: WO91/06524

PCT Pub. Date: May 16, 1991

[30] Foreign Application Priority Data

Nov. 2, 1989 [DE] Fed. Rep. of Germany ....... 3936399

[51] Int. Cl.$^5$ ............................................. C07C 45/54
[52] U.S. Cl. ................................................... 568/319
[58] Field of Search ................. 568/319, 322, 323; 560/86

[56] References Cited

U.S. PATENT DOCUMENTS

| 4,827,041 | 5/1989 | Ford et al. | 568/322 |
| 5,041,616 | 8/1991 | Sumner | 568/319 |

FOREIGN PATENT DOCUMENTS

| 0057503 | 11/1982 | European Pat. Off. | 568/319 |
| 0075390 | 3/1983 | European Pat. Off. | 568/319 |
| 0675389 | 3/1983 | European Pat. Off. | 568/319 |
| 0232992 | 8/1987 | European Pat. Off. | 568/319 |

OTHER PUBLICATIONS

Blicke, F. F., et al, *J. Am. Chem. Soc.* 60:2283-2285 (1938).

*Primary Examiner*—James H. Reamer
*Attorney, Agent, or Firm*—Connolly and Hutz

[57] ABSTRACT

A process for the preparation of 1,4-bis(4-hydroxybenzoyl)benzene of the formula (I)

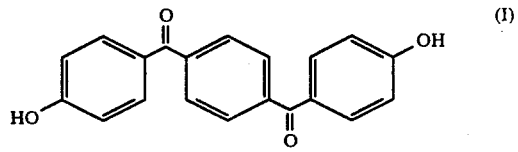

by rearranging diphenyl terephthalate of the formula (II)

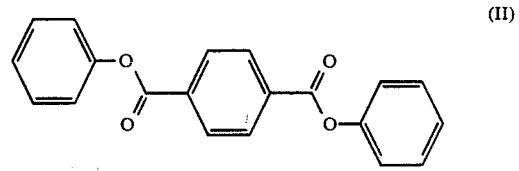

in about 3 to about 50 parts, relative to the diphenyl terephthalate, of an anhydrous organic solvent which is inert to the reactants, in the presence of about 30 to about 500 mol-% of a haloalkanesulfonic acid (catalyst) of the general formula (III) or (IV)

$$Y(C_nX_{2n})SO_3H \qquad (III)$$

$$Y(C_nF_{2n})SO_3H \qquad (IV)$$

in which Y is a fluorine or hydrogen atom, and X is a fluorine and/or chlorine atom, with the proviso that at least one X is a fluorine atom, and n is an integer from 1 to 10, at temperatures of about 10° to about 200° C.

16 Claims, No Drawings

PROCESS FOR THE PREPARATION OF 1,4-BIS(4-HYDROXYBENZOYL)BENZENE

The invention relates to a process for the preparation of 1,4-bis(4-hydroxybenzoyl)benzene by Fries rearrangement of diphenyl terephthalate in the presence of haloalkanesulfonic acid in solvents.

In J.A.C.S. 1938, p. 2283, Blicke et al. describe the rearrangement of diphenyl terephthalate in the presence of AlCl$_3$ in carbon disulphide (CS$_2$). After distilling off the solvent, the reaction mixture is heated to 185°–190° C. Following destruction of the aluminum complex with dilute hydrochloric acid, the product obtained is extracted with dilute aqueous sodium hydroxide solution. Final acidification then gives 1,4-bis(4-hydroxybenzoyl)benzene, which has a melting point of 297°–299° C. after recrystallization from alcohol. However, this synthesis route is unsuitable for industrial production because of disadvantages associated therewith, such as aluminum-containing wastewater and a plurality of side reactions owing to the considerably elevated temperature.

A process for the preparation of 1,4-bis(4-hydroxybenzoyl)benzene is known from EP 0,075,390 in which the target compound is prepared starting from phenol and terephthalic acid in fluoroalkanesulfonic acid as a solvent.

There was therefore a need for a process in which the catalyst system can be used in sub-stoichiometric amounts, easily worked up and recovered.

It has now been found that 1,,4-bis(4-hydroxybenzoyl)benzene of the formula I

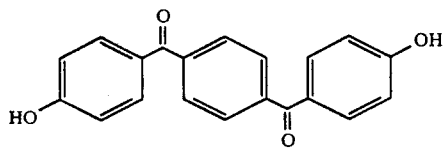

can advantageously be prepared by rearranging diphenyl terephthalate of the formula II

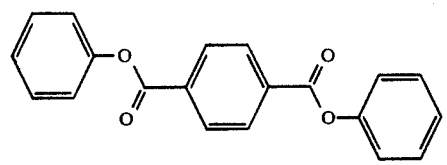

in about 3 to about 50 parts, preferably about 5 to about 20 parts, relative to the diphenyl terephthalate, of an anhydrous organic solvent which is inert to the reactants, in the presence of haloalkanesulfonic acids (catalysts) of the general formula III

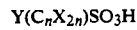

preferably of the general formula IV

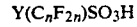

in which Y is a fluorine or hydrogen atom, and X is a fluorine and/or chlorine atom, with the proviso that at least one X is a fluorine atom, and n is an integer from 1 to 10, at temperatures of about 10° C. to about 200° C., preferably of about 80° C. to about 130° C.

It is advantageous in the process according to the invention to work under oxygen-free conditions. As far as the pressure conditions are concerned, the reaction can be carried out at atmospheric pressure or alternatively at a slight overpressure, in particular at the autogenous pressure of the system, which is determined in particular by the temperature used, but also by other factors, such as the extent of filling of the reaction vessel. For example, the overpressure can be in the range up to 10 or 15 bar. If working at elevated pressure, the process can be carried out, for example, in a stainless steel autoclave, which if desired is coated with a resistant material, such as, for example, polytetrafluoroethylene. The reaction can be accelerated by the use of overpressure, but an increased formation of by-products can also be associated with this.

An advantage of the process according to the invention is that diphenyl terephthalate or phenol/terephthaloyl dichloride is added to the mother liquor obtained after the separation of the precipitated 1,4-bis(4-hydroxybenzoyl)benzene and thus the reaction medium can be reused many times, for example up to six times, without noticeable losses of yield occurring. In the case of too frequent recycling, concentration of by-products is observed so that it proves to be convenient to exclude about 20% by weight and to fortify with fresh catalyst. The excluded mother liquor can be worked up externally by known processes in order to recover the catalyst. A second possibility for working-up is the concentration of the reaction mixture by distilling off the solvent/catalyst mixture, which can likewise be fed back into the next reaction. Which of the two methods proves the most favorable depends on the solvent used and the haloalkanesulfonic acid employed. The crude 1,4-bis(4-hydroxybenzoyl)benzene separated off can be purified by treatment with alkali metal hydroxides and subsequent pH-controlled acidification and separated off from the co-formed half ester, which is fed back into the next reaction.

The catalysts used according to the invention of the said formula (III) preferably contain not more than 3 chlorine atoms, in particular at most one chlorine atom. The group $C_nX_{2n}$ or $C_nF_{2n}$ n can be straight-chain or branched, compounds in which Y is a hydrogen atom frequently containing this in the β-position.

The perfluorinated catalysts used according to the invention are known (cf. DE-OS 2,139,994), as are the β-H-perfluoroalkanesulfonic acids (J. Am. Chem. Soc. 75, 44595–44596, 1953). If they are not known, they can be obtained by the customary processes. Suitable compounds of the said general formula (III) are, for example, perfluoro-n-octanesulfonic acid, perfluorohexanesulfonic acid, perfluorobutanesulfonic acid, pentafluoroethanesulfonic acid, β-H-perfluoroheptanesulfonic acid and β-H-perfluoropentanesulfonic acid. Mixtures of various catalysts can also be used. Trifluoromethanesulfonic acid, 2-chloro-1,1,2-trifluoroethanesulfonic acid and 2-hydroperfluoropropanesulfonic acid are preferred.

In general, the catalyst is added to the first batch in amounts of about 30 to about 500 mol-%, relative to the diphenyl terephthalate. If the mother liquor after separating off the desired reaction product or the solvent/catalyst mixture distilled off is used again, by recycling it, as a rule a sub-stoichiometric amount of catalyst is used as a result.

Inert organic solvents which can be employed are, for example, chlorobenzene, o-dichlorobenzene, m-dichlorobenzene, o-chlorotoluene, nitrobenzene, N-methylpyrrolidone or sulfolane.

The rearrangement can also be carried out in a one-pot process, starting from phenol and terephthaloyl dichloride, without intermediate isolation of the diphenyl terephthalate, the initial esterification being carried out at temperatures of about 10° to about 200° C. In this procedure as well, phenol/terephthaloyl dichloride can be added to the reaction mixture obtained after completion of the rearrangement after separating off the 1, 4-bis (4-hydroxybenzoyl) benzene precipitated and the mixture can be reused.

The 1,4-bis(4-hydroxybenzoyl)benzene of the said formula (I) obtained by the process according to the invention is an important monomer for chemical-resistant plastics which are still resistant even at high temperatures. If necessary, the compound of the formula (I) can be recrystallized from solvents, such as, for example, ethanol.

The invention is illustrated by the examples below without being limited thereto. In these examples h is hour and BHB is 1,4-bis(4-hydroxybenzoyl)benzene.

EXAMPLES

1.) 0.25 mol of diphenyl terephthalate and 0.25 mol of hexafluoropropanesulfonic acid are heated at 100°-110° C. for 10 h in 300 ml of chlorobenzene. After stirring until cold, the BHB precipitated is filtered off and washed with 50 ml of chlorobenzene, and the crude product is dried. The mother liquor can be fed back into the next reaction.

Yield: 85% of theory.
Purity (HPLC) 92%.
M.p.: 312°-3150° C.

If the same amount of o-dichlorobenzene, m-dichlorobenzene or o-chlorotoluene is used instead of 300 ml of chlorobenzene and the reaction is otherwise carried out as indicated in this example, virtually the same result is thus attained.

If the same molar amount of trifluoromethanesulfonic acid, perfluorobutanesulfonic acid or 2-chloro-1,1,2-trifluoroethanesulfonic acid is used instead of 0.25 mol of hexafluoropropanesulfonic acid and the reaction is otherwise carried out as indicated in this example, virtually the same result is thus achieved.

2.) 0.5 mol of phenol, 0.25 mol of terephthaloyl dichloride and 0.50 mol of hexafluoropropanesulfonic acid are initially introduced into 500 ml of nitrobenzene at room temperature and the mixture is stirred at the stated temperature while hydrogen chloride is evolved. After evolution of gas is complete, the mixture is heated to 80° C. and highly heated to 100° C. in the course of 2 h and stirred for 8 h. After stirring until cold, precipitated BHB is filtered off and washed with 50 ml of nitrobenzene, and the crude product is dried. The mother liquor can be fed back into the next reaction.

Yield: 80-85% of theory.
Purity (HPLC) 90-92%.
M.p.: 312°-314° C.

3.) 0.5 mol of phenol, 0.25 mol of terephthaloyl dichloride and 0.5 mol of trifluoromethanesulfonic acid are initially introduced into 500 ml of nitrobenzene at room temperature and the mixture is stirred at the stated temperature for 3 h while hydrogen chloride is evolved. After evolution of gas is complete, the mixture is heated to 80° .C and stirred for a further 10 h. The reaction mixture is then concentrated in a medium high vacuum (0.1 mbar) at 100° C. to a fifth of the volume. The resulting distillate can be reused for the next reaction. The residue is diluted with 200 ml of acetone and stirred into 1 l of water, and the crude product precipitating in this way is filtered off.

Purification is Carried Out as Follows

The solid is washed with 200 ml of sodium hydrogencarbonate (10% strength) and dissolved in 2.5 l of a 0.2 N $K_2CO_3$ solution. The half ester formed as a by-product is precipitated by slow acidification of the solution with hydrochloric acid to pH 8.5 and is separated off by filtration. The product is precipitated by further acidification to pH 6.

Yield: 75% of theory.
Purity (HPLC): 96%.
M.p.: 317°-318° C.

We claim:

1. A process for the preparation of 1,4-bis(4-hydroxybenzoyl)benzene of the formula (I)

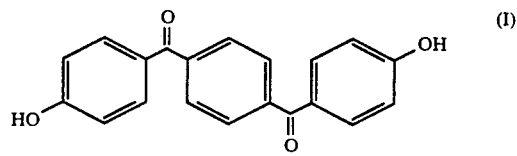

which comprises rearranging diphenyl terephthalate of the formula (II)

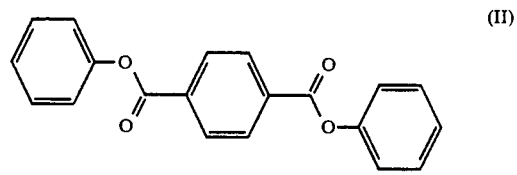

in about 3 to about 50 parts, relative to the diphenyl terephthalate, of an anhydrous organic solvent which is inert to the reactants, in the presence of about 30 to about 500 mol-% of a haloalkanesulfonic acid (catalyst) of the general formula (III) or (IV)

$Y(C_nX_{2n})SO_3H$ (III)

$Y(C_nF_{2n})SO_3H$ (IV)

in which Y is a fluorine or hydrogen atom, and X is a fluorine and/or chlorine atom, with the proviso that at least one X is a fluorine atom, and n is an integer from 1 to 10,, at temperatures of about 10° to about 200° C.

2. The process as claimed in claim 1, wherein the rearrangement is carried out at temperatures of about 50° C. to about 160° C.

3. The process as claimed in claim 1, wherein the rearrangement is carried out at temperatures of about 80° C. to about 130° C.

4. The process as claimed in claim 1, wherein Y in the general formulae (III) or (IV) is a hydrogen atom and this is in the β-position to the —$SO_3H$ group.

5. The process as claimed in claim 1, wherein the rearrangement is carried out in the presence of hexafluoropropanesulfonic acid or trifluoromethanesulfonic acid.

6. The process as claimed in claim 1, wherein the rearrangement is carried out in chlorobenzene, dichlorobenzene, chlorotoluene, nitrobenzene, N-methylpyrrolidone or sulfolane as inert organic solvent.

7. The process as claimed in claim 1, wherein the rearrangement is carried out in about 5 to about 20 parts of the inert organic solvent, relative to the diphenyl terephthalate.

8. The process as claimed in claim 1, wherein the rearrangement of the diphenyl terephthalate is carried out in the pressure range from atmospheric pressure up to the autogenous pressure of the reaction mixture under the reaction conditions used.

9. The process as claimed in claim 1, wherein the rearrangement is carried out in the pressure range from atmospheric pressure up to about 15 bar.

10. The process as claimed in claim 1, wherein the rearrangement is carried out in the absence of oxygen.

11. The process as claimed in claim 1, wherein the mother liquor obtained after separating off the 1,4-bis(4-hydroxybenzoyl)benzene is reused.

12. The process as claimed in claim 1, wherein diphenyl terephthalate is added to the reaction mixture obtained after completion of the rearrangement after separating off the 1,4-bis(4-hydroxybenzoyl)benzene and the mixture is reused.

13. The process as claimed in claim 1, wherein the rearrangement is carried out in a one-pot process, starting from phenol and terephthaloyl dichloride, without intermediate isolation of the diphenyl terephthalate, the initial esterification being carried out at temperatures of about 10° to about 200° C.

14. The process as claimed in claim 13, wherein phenol/terephthaloyl dichloride is added to the reaction mixture obtained after completion of the rearrangement after separating off the 1,4-bis(4-hydroxybenzoyl)benzene and the mixture is reused.

15. The process as claimed in claim 1, wherein the haloalkanesulfonic acid (catalyst( is of formula (IV).

16. The process as claimed in claim 1, wherein formula (III) contains between 1 and 3 chlorine atoms.

* * * * *